United States Patent [19]

Schulze et al.

[11] Patent Number: 4,904,462
[45] Date of Patent: Feb. 27, 1990

[54] MULTIPLY-TRITIATED STEROIDAL-20,17-SPIROLACTONES AND THEIR USE AS TRACER COMPOUNDS

[75] Inventors: Paul-Eberhard Schulze; Klaus Nickisch; Henry Laurent, all of Berlin; Kunhard Pollow, Mainz-Hechtsheim, all of Fed. Rep. of Germany

[73] Assignee: Schering Aktiengesellschaft, Berlin and Bergkamen, Fed. Rep. of Germany

[21] Appl. No.: 722,255

[22] Filed: Apr. 12, 1985

[30] Foreign Application Priority Data

Apr. 13, 1984 [DE] Fed. Rep. of Germany ....... 3414508

[51] Int. Cl.$^4$ ...................... A61K 49/02; A61K 31/58
[52] U.S. Cl. ......................... 424/1.1; 540/13; 540/41; 514/175
[58] Field of Search .................. 424/1.1; 514/175; 540/23, 41

[56] References Cited

U.S. PATENT DOCUMENTS 3,855,208 12/1974 Rutner et al. .................... 424/1.1 X
3,966,714 6/1976 Philippson ...................... 260/239.57
4,450,107 5/1984 Nickisch et al. .................. 540/15
4,559,331 12/1985 Nickisch et al. .................. 540/42 X Primary Examiner—John S. Maples
Attorney, Agent, or Firm—Millen, White & Zelano

[57] ABSTRACT

Novel, multiple-tritiated steroid-20,17-spirolactones of general Formula I

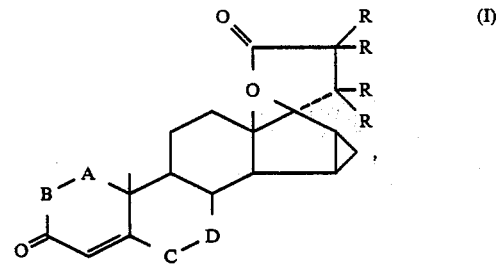

wherein
—A—B— is —$CH_2$—$CH_2$—, —CH=CH— or

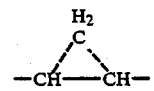

and
—C—D— is

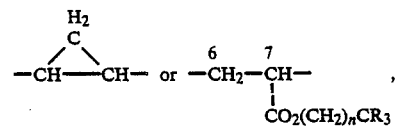

R is hydrogen or tritium and
n is 0 or 1, are usable as tracer materials for the detection of mineralocorticoid receptors.

13 Claims, No Drawings

MULTIPLY-TRITIATED STEROIDAL-20,17-SPIROLACTONES AND THEIR USE AS TRACER COMPOUNDS

BACKGROUND OF THE INVENTION

This invention relates to new compounds having valuable pharmacological and radiological properties.

The mineralocorticoid aldosterone is a participant, inter alia, in the regulation of renal excretion in man. An increase in aldosterone secretion leads primarily to a retention of sodium ions and secondarily to water retention with simultaneous excretion of potassium. Water and sodium chloride retention due to increased aldosterone activity is, inter alia, the cause of edema formations in cirrhosis of the liver, decompensated cardiac insufficiency and nephrotic syndrome.

It is assumed that the first stage in the molecular effect of aldosterone at the level of the target cell is the binding to a specific cytosol receptor. This complex is translocated into the cell nucleus, the seat of the genetic apparatus, and is bound in the cell nucleus to chromatin by way of specific acceptor regions. This binding to chromatin leads to the so-called gene activation with the result of a change in the growth and function of the target cell. If an aldosterone antagonist, inhibiting this behavior in the cellular region, is supplied to the organism, then the effect of aldosterone can be neutralized. Flushing out of the edema can be achieved in the aforementioned pathological conditions.

The technique of using tritium-labeled aldosterone as a tracer for the detection of mineralocorticoid receptors and also for determining the affinity of aldosterone antagonists to the mineralocorticoid receptors has been known for some time. Prorenone also has been utilized for this purpose (M. Claire et al., Proc. of the Searle Symposium, Nice 1978, pp. 67–69).

However, aldosterone, as a specific ligand for mineralocorticoid receptor testing, exhibits several disadvantages. Aldosterone, as as natural ligand, is metabolized under in vitro conditions of receptor testing by enzyme systems inherent in the cell; the metabolites can decisively interfere with the receptor test system. Aldosterone binds, with a relative binding affinity (so-called RBA value) of 6% with respect to cortisol, to the human serum protein CBG, leading to falsifications of the test result since serum contaminations are unavoidable in the framework of cytosol-type receptor preparations. Aldosterone exhibits a relative binding affinity in rat liver cytosol of 30% with respect to dexamethasone, a synthetic ligand for glucocorticoid receptor analysis. This renders discrimination between mineralocorticoid and glucocorticoid receptors extremely difficult, especially since the kidney as the target organ of aldosterone activity has ten times more glucocorticoid receptor than mineralocorticoid receptors.

SUMMARY OF THE INVENTION

Accordingly, it is an object of the present invention to provide radioactively labeled ligands useful for the analysis of mineralocorticoid receptors, the binding capacities of which to the mineralocorticoid receptor are highly specific while binding to other receptor proteins (e.g. progesterone and glucocorticoid receptor) as well as to CBG is negligible.

It is another object of this invention to provide such a ligand radioactively labeled for receptor testing which is stable metabolically.

Upon further study of the specification and appended claims, further objects and advantages of this invention will become apparent to those skilled in the art.

These objects have been attained by providing multiply-tritiated steroidal-20,17-spirolactones of Formula I

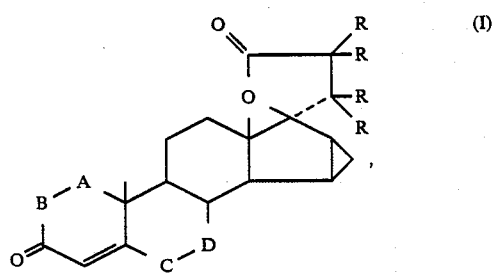

wherein

—A—B— is —CH$_2$—CH$_2$—, —CH=CH— or

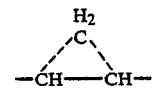

and
—C—D— is

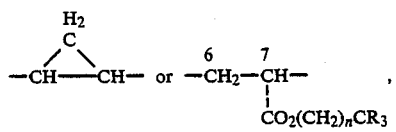

R is hydrogen or tritium and
n is 0 or 1.

These compounds overcome the mentioned disadvantages and are stable metabolically under the conditions of the receptor test.

DETAILED DISCUSSION

The table illustrates the relative binding affinities for aldosterone and prorenone as well as compounds of this invention with respect to the mineralocorticoid, glucocorticoid and progesterone receptor as well as CBG.

The compounds of this invention exhibit a binding affinity that is higher by a large multiple for the mineralocorticoid receptor, as compared with a strongly reduced, partially equal, partially lacking affinity with respect to glucoccorticoid and progesterone receptors, respectively, and CBG.

TABLE
Relative Binding Affinities of Aldosterone and Aldosterone Antagonists With Respect to Mineralocorticoid, Glucocorticoid and Progesterone Receptors As Well As Serum CBG
| LIGAND | Mineralo-corticoid Receptor | Gluco-corticoid Receptor | Progesterone Receptor | CBG |
|---|---|---|---|---|
| Aldosterone | 100 | 30 | 0.2 | 6 |
| Prorenone | 200 | 3 | 32 | <0.01 |
| Example 3 | 90 | 0.9 | 50 | <0.1 |
| Example 4 | 400 | 0.8 | 0.5 | <0.1 |
| Example 6 | 600 | 0.4 | 0.2 | <0.1 |
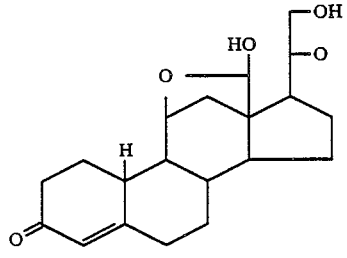
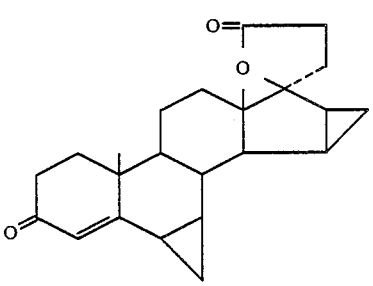
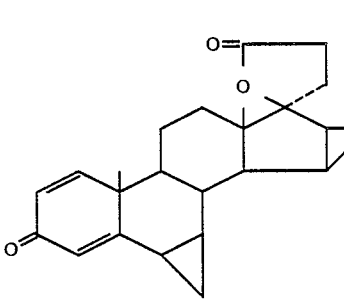
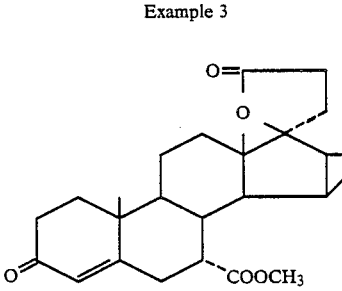
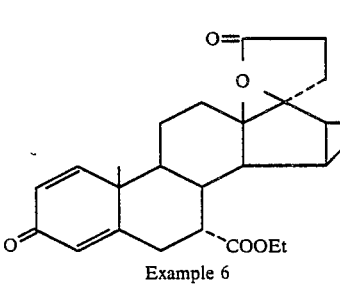

TABLE-continued

Relative Binding Affinities of Aldosterone and Aldosterone Antagonists With Respect to Mineralocorticoid, Glucocorticoid and Progesterone Receptors As Well As Serum CBG

| LIGAND | Mineralo-corticoid Receptor | Gluco-corticoid Receptor | Progesterone Receptor | CBG |
|---|---|---|---|---|
| 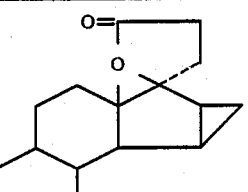 Example 7 | 600 | 0.2 | 0.2 | <0.1 |
| 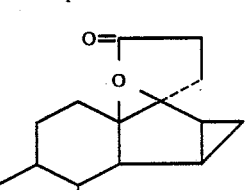 Example 8 | 800 | 0.8 | 0.95 | <0.1 |

The values in the table were conventionally obtained as follows:

The relative binding affinities (RBA values) of aldosterone, prorenone as well as the compounds of this invention were determined, for the progesterone receptor, in human uterus cytosol, for the glucocorticoid receptor, in liver cytosol, and for the mineralocorticoid receptor, in the kidney cytosol of adrenalectomized rats. The relative binding affinity with respect to CBG was measured in the serum of pregnant women, diluted 1:30.

The procedure for the receptor analysis was as follows:

Cytosol from human uterus, rat kidneys and rat livers was prepared by homogenizing the tissues under cooling with the addition of receptor-stabilizing buffer (10 mmol/l of KH$_2$PO$_4$, 10 mmol/l of K$_2$HPO$_4$, 1.5 mmol/l of EDTA, 3 mmol/l of NaN$_3$, 5 mmol/l of monothioglycerol, 10% glycerol, pH 7.5). The homogenate was then centrifuged for 30 minutes at 105,000×g. The thus-formed supernatant centrifugation liquor corresponds to the tissue cytosol utilized for receptor testing. Then, in each case, 50 μl of a $^3$H-steroid ($^3$H-R5020) for progesterone receptor testing, $^3$H-dexamethasone for glucocorticoid receptor testing, $^3$H-aldosterone for mineralocorticoid receptor testing), dissolved in a buffer, was pipetted into test tubes (final concentration 8 nmol/l). Thereafter, the various steroids to be tested (in respectively six different concentrations: $10^{-10}$ to $10^{-5}$ mol/l) in 50 μl of buffer were added to the incubating tubes. Finally, 100 μl of cytosol was introduced into each tube by pipetting, and the incubation batch was thoroughly mixed and incubated overnight at 0°-4° C. Incubation was terminated by adding 0.5 ml of dextran-layered activated carbon (DCC) in a buffer. After 10 minutes of incubation under cooling, DCC was removed by centrifuging and thus the free, not receptor-bound steroid was separated from the receptor-bound steroid. The radioactivity was measured in the supernatant centrifugation liquors by means of a scintillation counter. All thus-determined values result from triple measurements. The measured dpm values were expressed in % of relative binding affinity, the RBA value referring to 50% displacement of the $^3$H-labeled ligand by its unlabeled authentic steroid (=100% RBA).

As for the RBA values, for CBG an analogous procedure was followed, using $^3$H-cortisol and a 1:30 dilution of the serum of pregnant women as the source of CBG.

The compounds of this invention are labeled by at least three tritium atoms. Labeling is effected on the substituent in the 7α-position and/or on the lactone ring in the 18,19-position.

Labeling with tritium on the substituent in the 7-position can be conducted according to methods known per se in connection with the corresponding 7α-hydroxycarbonyl compounds (DOS 3,111,951 and 3,330,084 and USP 4,450,107 and U.S. application Ser. No. 641,599 now U.S. Pat. No. 4,599,331) tritium-labeled alkyl halogenide and silver oxide in dimethylformamide.

Labeling with tritium in the 18,19-position on the lactone ring can occur by tritiation with tritium gas of the corresponding 17α-hydroxypropynyl compound in a protonic solvent, such as 2-propanol, in the presence of palladium, and subsequent oxidation and lactonization with chromic acid/pyridine complex, analogously to the method described, e.g., in U.S. Pat. No. 3,966,714.

The compounds of this invention have the advantage that their specific activity, often >100 Ci/mmol, is relatively high and that they are stable chemically as well as biologically.

The compounds of this invention can be formulated and used fully analogously to known agents for mammals including humans, in tests for detection and/or analysis of mineralocorticoid receptors, in vitro or in vivo, e.g., analogously to 3H-aldosterone (Dupont, New England Nuclear, Boston, Mass.). Such tests are conducted as described above or otherwise fully conventionally as disclosed in *Principles of Receptorology*, edited by M. K. Agawal, Walter De Gruyter and Co., Berlin, 1983, see especially G. Wambach and W. Kaufmann, *Mineral Corticoids Receptors*, pages 105–139.

When the compounds of this invention are used in vivo, the formulations are fully conventional, analogously to the known aldosterone-antagonist spironolactone. The dosage of the compounds of this invention for administration, e.g., to human subjects is 10–200 mg/day. In terms of body weight, suitable dosages are 0.1–3 mg/day.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The following examples demonstrate the preparation of the compounds of this invention.

EXAMPLE 1

A solution of 5 mg of 7α-hydroxycarbonyl-15β,16β-methylene-3-oxo-17α-pregn-4-ene-21,17-carbolactone in 100 μl of dimethylformamide is combined with 5 mg of silver oxide and, under a high vacuum, 8 μg of [$^3H_3$]-methyl iodide (about 80–90 Ci/mmol) is additionally introduced. The mixture is agitated at room temperature for 2 hours on a shaker, saturated sodium chloride solution is added, and the mixture is extracted with dichloromethane. The dichloromethane solution is applied, after concentration, to analytical HPTLC plates and developed in the mobile phase system chloroform/acetone 9:1. After elution of the desired zone with dioxane, the product is once more purified with semipreparative HPLC, thus obtaining 7α-($^3H_3$)methoxycarbonyl-15β,16β-methylene-3-oxo-17α-pregn-4-ene-21,17α-carbolactone. The specific activity of the pure material corresponds to that of ($^3H_3$)-methyl iodide (76.4 Ci/mmol).

EXAMPLE 2

(a) In a small 1 ml flask, 1.00 mg of 17α-(3-hydroxyl-1-propynyl)-6β,7β15β,16β-dimethylene-5β-androstane-3β,5,17β-triol is dissolved in 100 μl of tetrahydrofuran and 650 μl of 2-propanol and combined with 5 mg of Pd/CaCO$_3$. The mixture is hydrogenated for one hour with gaseous tritium, diluted with methanol, suctioned off from the catalyst, and concentrated. The crude 17α-(3-hydroxy-[2',3'-$^3H_4$]propyl)-6β,7β;15β,16β-dimethylene-5β-androstane-3β,5,17β-triol (II) is tested for purity in a TLC system chloroform/acetone 8:2, and the specific activity is determined by means of UV and radioactivity measurement by way of HPLC to be >100 Ci/mmol.

(b) 1.00 mg of crude II is dissolved in 500 μl of dimethylformamide and combined under agitation and water cooling with 3.00 mg of pyridinium dichromate in two portions. The mixture is further stirred for 30 minutes and then for 24 hours at 70° C. The cooled reaction solution is stirred into about 6 ml of ethyl acetate, suctioned off over sodium sulfate from the thus-precipitated chromium salts, and washed thoroughly with ethyl acetate. The ethyl acetate phase is washed three times with water, the washing water is reextracted with ethyl acetate, combined, and washed once with saturated sodium chloride solution. After drying over sodium sulfate and evaporation, about 1 mg of crude 6β,7β;15β,16β-dimethylene-3-oxo-17α-(18,19-$^3H_4$)pregn-4-ene-21,17-carbolactone is obtained. The product is purified by semipreparative HPLC, and the specific activity is determined to be >100 Ci/mmol (420 μg).

EXAMPLE 3

411 μg of 6β,7β;15β,16β-dimethylene-3-oxo-17α-(18,19-$^3H_4$)pregn-4-ene-21,17-carbolactone is heated in 100 μl of dioxane to 80°–90° C. and 400 μg of dichlorodicyanobenzoquinone is added thereto. The reaction solution is then shaken for 90 minutes at a bath temperature of 100° C. and then cooled in an ice bath, suctioned off from the separated hydroquinone, thoroughly washed with dioxane, and the filtrate extensively concentrated under vacuum. The residue is taken up in ethyl acetate and separated by means of semipreparative HPLC, thus obtaining 225 μg of 6μ,7β;15β,16β-dimethylene-3-oxo-17α-[18,19-$^3H_4$]pregna-1,4-diene-21,17-carbolactone (IV) having a specific activity of 104 Ci/mmol.

EXAMPLE 4

Analogously to Example 1, 7α-hydroxycarbonyl-15β,16β-methylene-3-oxo-17α-(18,19-$^3H_4$)pregn-4-ene-21,17-carbolactone is reacted with [$^3H_3$]-methyl iodide, thus obtaining 7α-($^3H_3$)methoxycarbonyl-15β,16β-methylene-3-oxo-17α-[18,19-$^3H_4$]pregn-4-ene-21,17-carbolactone with a specific activity of 181.4 Ci/mmol.

EXAMPLE 5

In analogy to Example 1, 7α-hydroxycarbonyl-15β,16β-methylene-3-oxo-17α-pregna-1,4-diene-21,17-carbolactone is reacted with [$^3H_3$]-methyl iodide, producing 7α-[$^3H_3$]methoxycarbonyl-15β,16β-methylene-3-oxo-17α-pregna-1,4-diene-21,17-carbolactone having a specific activity corresponding to that of the [$^3H_3$]-methyl iodide employed.

EXAMPLE 6

Analogously to Example 1, 7α-hydroxycarbonyl-15β,16β-methylene-3-oxo-17α-pregna-1,4-diene-21,17-carbolactone is reacted with 1-[$^3H_3$]-ethyl iodide, thus obtaining 7α-[1'-($^3H_3$)ethoxy]carbonyl-15β,16β-methylene-3-oxo-17α-pregna-1,4-diene-21,17-carbolactone having a specific activity corresponding to that of the 1-[$^3H_3$]-ethyl iodide utilized.

EXAMPLE 7

In analogy to Example 2, 1α,2α;15β,16β-dimethylene-7α-methoxycarbonyl-3-oxo-17α-[18,19-$^3H_4$]pregn-4-ene-21,17-carbolactone having a specific activity of 104 Ci/mmol is obtained from 17α-(3-hydroxy-1-propynyl)-1α,2α;15β,16β-dimethylene-7α-methoxycarbonyl-3-oxo-androsten-17β-ol by way of the intermediate stage of 17α-(3-hydroxy-[2',3'-$^3H_4$]-propyl)-1α,2α;15β,16β-dimethylene-7α-methoxycarbonyl-3-oxo-4-androsten-17β-ol.

EXAMPLE 8

Analogously to Example 1, 7α-hydroxycarbonyl-15β,16β-methylene 3-oxo-17α-pregn-4-ene-21,17-carbolactone is reacted with 1-[³H₃]-ethyl iodide, thus producing 7α-[1'-(³H₃)-ethoxy]carbonyl-15β,16β-methylene-3-oxo-17α-pregn-4-ene-21,17-carbolactone having a specific activity corresponding to that of the 1-[³H₃]-ethyl iodide employed.

EXAMPLE 9

10.0 mg of 7α-(³H₃)methoxycarbonyl-15β,16β-methylene-3-oxo-17α(18,19-³H₄)-pregn-4-ene-21,17-carbolactone is micronized (finely ground) and homogeneously mixed with:

80.0 mg lactose (DAB (German Pharmacopoeia 7), USP XVII),
29.6 mg microcrystalline cellulose, and
0.4 mg magnesium stearate (USP XVII)

and compressed into tablets without previous granulation, these tablets having a weight of 120 mg, with a diameter of about 7 mm and a thickness of 2.7-2.9 mm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A multiple-tritiated steroid-20,17-spirolactone of the formula

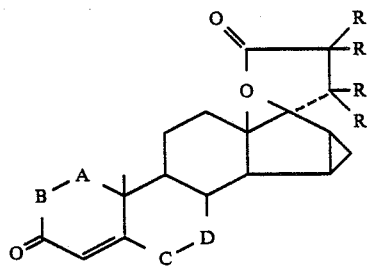

wherein
—A—B— is —CH₂—CH₂—, —CH=CH— or

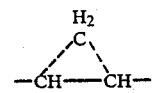

and
—C—D— is

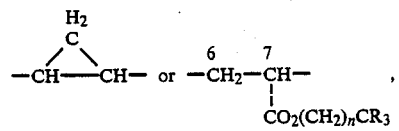

R is hydrogen or tritium and
n is 0 or 1,
with the proviso that at least three R-groups are tritium.

2. A compound of claim 1 wherein the three R groups on the 7-position are tritium.

3. A compound of claim 1 wherein the four R-groups in the 18,19-positions are tritium.

4. A compound of claim 1 wherein —C—D— is

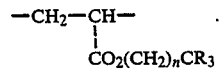

5. 7α-(³H₃)Methoxycarbonyl-15β,16β-methylene-3-oxo-17α-pregn-4-ene-21,17-carbolactone, a compound of claim 1.

6. 6β,7β;,5β,16β-Dimethylene-3-oxo-17α-(18,19-³H₄)pregn-4-ene-21,17-carbolactone, a compound of claim 1.

7. 6β,7β;;15β,16β-Dimethylene-3-oxo-17α-(18,19-³H₄)pregna-1,4-diene-21,17-carbolactone, a compound of claim 1.

8. 7α-(³H₃)Methoxycarbonyl-15β,16β-methylene-3-oxo-17α-[18,19-³H₄]pregn-4-ene-21,17-carbolactone, a compound of claim 1.

9. 7α-(³H₃)Methoxycarbonyl-15β,16β-methylene-3-oxo-17a-pregna-1,4-diene-21,17-carbolactone, a compound of claim 1.

10. 7α-[1'-(₃H₃)Ethoxy]carbonyl-15β,16β-methylene-3-oxo-17α-pregna-1,4-diene-21,17-carbolactone, a compound of claim 1.

11. 1α,2α15β,16β-Dimethylene-7α-methoxycarbonyl-3-oxo-17α-[18,19-³H₄]pregn-4-ene-21,17-carbolactone, a compound of claim 1.

12. 7α-[1'-(₃H₃)Ethoxy]carbonyl-15β,16β-methylene-3-oxo-17α-pregn-4-ene-21,17-carbolactone, a compound of claim 1.

13. A pharmaceutical composition comprising an amount of a compound of claim 1 and a pharmaceutically acceptable carrier.

* * * * *